United States Patent [19]

Bálint et al.

[11] Patent Number: 4,776,874

[45] Date of Patent: Oct. 11, 1988

[54] 2-CHLORO-ETHYL PHOSPHONIC ACID ESTERS AND PLANT GROWTH REGULATING AGENTS CONTAINING SAME AS ACTIVE INGREDIENT

[75] Inventors: Sándor Bálint, Veszprém; Judit Benczik née Pásztor, Balatonalmádi; József Fodor, Veszprém; András Horváth, Balatonfüzfő-Gyártelep; Elemér Tömördi; Csaba Söptei, both of Veszprém; József Karsai, Velence; Endre Sebestyén, Agárd; Sándor Gaál, Szigethalom; Iván Gárdi; György Kiss, both of Budapest; András Papp, Törökbálint; Imre Csatlós, Hódvezővásárhely, all of Hungary

[73] Assignee: Nitrokémia Ipartelepek, Füzfőgyártelep, Hungary

[21] Appl. No.: 839,498

[22] PCT Filed: Jul. 17, 1985

[86] PCT No.: PCT/HU85/00043

§ 371 Date: Mar. 13, 1986

§ 102(e) Date: Mar. 13, 1986

[87] PCT Pub. No.: WO86/00903

PCT Pub. Date: Feb. 13, 1986

[30] Foreign Application Priority Data

Jul. 18, 1984 [HU] Hungary ................... 2801/84

[51] Int. Cl.$^4$ ................... A01N 57/24; C07F 9/40
[52] U.S. Cl. ................... 71/86; 549/220
[58] Field of Search ................... 549/220; 71/86

[56] References Cited

U.S. PATENT DOCUMENTS 4,042,370  8/1977  Trueb ................... 71/86
4,560,682 12/1985  Hiroki et al. ................... 514/100
4,668,274  5/1987  Bálint et al. ................... 549/220 X

OTHER PUBLICATIONS

Houben–Weyl, Methoden der Organischen Chemie, vol. 12/1 (1963) pp. 417, 418, 423 & 424.

*Primary Examiner*—Richard L. Raymond
*Attorney, Agent, or Firm*—Schweitzer & Cornman

[57] ABSTRACT

The present invention relates to new compounds of the general formula (I)

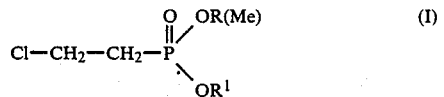

wherein
R stands for hydrogen, $C_{1-8}$ straight or branched chained alkyl, $C_{1-4}$ haloalkyl, $C_{1-4}$ alkoxy-$C_{1-2}$ alkyl,
$R^1$ stands for 2,3-dihydro-2,2-dimethyl-benzofuran-7-yl, 4-methyl-coumarin-7-yl, 2,2,4-trimethyl-(2H)-chromen-5-yl or 2,2,4-trimethyl-(2H)-chromen-7-yl and Me stands for a monovalent cation and represents the salt of the acid.

The new compounds show plant growth regulating activity and can be used as active ingredient of plant growth regulators.

6 Claims, No Drawings

2-CHLORO-ETHYL PHOSPHONIC ACID ESTERS AND PLANT GROWTH REGULATING AGENTS CONTAINING SAME AS ACTIVE INGREDIENT

The present invention relates to 2-chloro-ethyl phosphonic acid esters of the general formula (I)

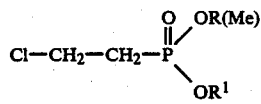

the preparation of said compounds as well as plant growth regulating agents containing as active ingredient the compounds of general formula (I).

In Hungarian patent specification No. 160,618 esters of 2-chloro-ethyl phosphonic acid with pyrocatechol, 4-chloro-pyrocatechol, phenol, salicylic alcohol, salicylic acid, resorcinol and other alcanols are disclosed. The biological activity of the esters is demonstrated on tomatoe, on bean arts, on ananas and on cereals.

In DD-PS No. 132,632 the alkoxy trichloromethyl esters of 2-halo-ethyl phosphonic acid are disclosed having plant growth regulating and desiccant activity.

In U.S. Pat. No. 4,042,370 the cyanoalkyl, alkoxycarbonyl-alkyl-alkinyl oxo and thio esters of 2-chloro-ethyl phosphonic acid are disclosed which are used for the treatment of rubber trees in order to increase latex crop. In J. Prakt. Chem. 1975 798–806 among others cyclic esters of 2-chloro ethyl phosphonic acid are disclosed and in these esters on the carbon attached to the oxygen can be hydrogen, alkyl or a cycloalkylene group can be attached to the two oxygen atoms.

The new 2-chloro-ethyl phosphonic derivatives can be characterised by the general formula (I) wherein R stands for hydrogen, $C_{1-8}$ straight or branched chained alkyl, $C_{1-4}$ haloalkyl, $C_{1-4}$ alkoxy-$C_{1-2}$ alkyl or a monovalent cation, $R^1$ stands for 2,3-dihydro-2,2-dimethyl-benzofuran-7-yl, 4-methyl-coumarin-7-yl, 2,2,4-trimethyl-(2H)-chromen-5-yl or 2,2,4-trimethyl-(2H)-chromen-7-yl, Me stands for a monovalent cation and represents the salt of the acid.

The new compounds show a plant growth regulating activity.

The compounds of the 2-chloro-ethyl-phosphonic acid esters can be prepared by reacting the corresponding benzofuran or coumarin or chromene derivative with 2-chloro-ethyl-phosphonic acid dichloride in the presence of an acid binding agent. When preparing the diesters the corresponding benzofuran, coumarin or chromene derivative and the alcanol are reacted in the presence of an acid binding agent, and the desired end-product is isolated by methods known per se.

The salts of the 2-chloro-ethyl phosphonic acid esters can be prepared by reacting the diester without isolation with the corresponding metal hydroxide.

From the active ingredients of the general formula (I) the usual compositions such as water-soluble concentrates, wetting agents, wettable powders, granules, emulsifyable concentrates, colloidal aqueous suspensions can be prepared.

The plant growth regulating activity means an activity of the active ingredient on the physiological processes of the plant growth depending on the time of the use, on the development stage of the plant and on the used concentration.

The compositions can be prepared by methods known per se such as admixing the active ingredients with carriers i.e. liquid solvents and/or solid carriers and optionally surfactants, such as emulsifying or dispersing agents can be used.

The compositions contain 0.1–95% by mass active ingredient. The active ingredients are usually used in the form of compositions or they can be used in the form of solutions, emulsifyable concentrates, suspensions, wettable powders, dusting agents or granules by spraying or vapourization. The active ingredient concentrations can be varied within a wide range depending on the character of the used active ingredients.

The new active ingredients and the compositions prepared from the active ingredients are illustrated in the following Examples.

EXAMPLE 1

Preparation of 2-chloro-ethyl-phosphonic acid-O-(2,3-dihydro-2,2-dimethyl-benzofuran-7-yl)-monoester (Compound No. 1)

To 70 ml. anhydrous benzene 16.42 g (0.1 mole) 2,3-dihydro-2,2-dimethyl-7-hydroxy-benzofuran and as acid binding agent 12.11 g. (0.1 mole) N,N-dimethylaniline are added whereafter 21.93 g. (0.12 mole) 2-chloro-ethyl-phosphonic acid dichloride are added dropwise to the reaction mixture at room temperature under stirring. The reaction mixture is then heated for 2 hours and the reaction is monitored by gas chromatographic analysis.

When the reaction is completed the mixture is cooled and at 20°–30° C. a solution of 5.6 g. (0.14 mole) sodium hydroxide in 30 ml. water is added dropwise and the mixture is heated for 2 hours. The reaction mixture is then cooled, the benzene layer is separated, dried above anhydrous sodium sulphate and benzene is distilled off in vacuo on a rotatory film evaporator. The residual yellowish, thick, oily substance is washed with hexane and its purity is checked by gas chromatography. $n_D^{25} = 1.5225$.

2-Chloro-ethyl-phosphonic acid-O-(4'-methylcoumarin-7'-yl)-ester is similarly prepared but 2,3-dihydro-2,2-dimethyl-7-hydroxy-benzofuran was replaced by 4-methyl-umbelliferon as starting material. The obtained product is a thick gummy product, $n_D^{24} = 1.5650$.

EXAMPLE 2

Preparation of 2-chloro-ethyl-phosphonic acid O-methyl-(2,3-dihydro-2,2-dimethyl-benzofuran-7-yl)-ester (Compound No. 2)

16.42 g. (0.1 mole) 2,3-dihydro-2,2-dimethyl-7-hydroxy-benzofuran, 12.11 g. (0.1 mole) dimethyl-7-hydroxy-benzofuran, 12.11 g. (0.1 mole) N,N-dimethylaniline and 21.93 g. (0.12 mole) 2-chloro-ethyl-phosphonic acid dichloride are reacted as disclosed in Example 1.

To the cooled reaction mixture 3.52 g. (0.11 mole) methanol and 12.11 g. (0.1 mole) N,N-dimethyl-aniline are added dropwise. The reaction mixture is then heated for 2 hours. The reaction is then monitored by gas chromatographic analysis. After cooling the reaction mixture the precipitated N,N-dimethyl-aniline-hydrochloride is filtered and the benzene solution is washed with diluted hydrochloric acid solution with aqueous sodium hydroxide solution and then with water. It is dried above anhydrous sodium sulphate and the solvent is distilled off in vacuo on a rotatory film evaporator.

Thus 15.76 g. orange, thick, oily liquid substance are obtained, $n_D^{25} = 1.5180$.

By using the reaction components of the following table compounds 3–10 can be prepared by the process disclosed in Examples 1 and 2.

| Compound No. 2 | 10% by mass |
| mixture of polyoxyethylene-alkyl-aryl-ether and alkyl-phenol alkoxalate (Emulsogen I-40, manufactured by Hoechst) | 5% by mass |
| toluene | 85% by mass |
| | 100% by mass |

| Number of the compound | Reaction component aliphatic alcohol | heterocyclic phenol | Compound of the general formula (I) R | $R^1$ | end product |
|---|---|---|---|---|---|
| 3 | 2-chloro-ethanol | 2,3-dihydro-2,2-dimethyl-7-hydroxy-benzofuran | Cl—CH$_2$—CH$_2$ | 2,3-dihydro-2,2-dimethyl-benzofuran-7-yl | 2-chloro-ethyl-phosphonic acid-O—methyl-O—(2,3-dihydro-2,2-dimethyl-benzofuran-7-yl)-ester |
| 4 | n-octyl-alcohol | 2,3-dihydro-2,2-dimethyl-7-hydroxy-benzofuran | C$_8$H$_{17}$— | 2,3-dihydro-2,2-dimethyl-benzofuran-7-yl | 2-chloro-ethyl-phosphonic acid-O—(2-chloro-ethyl)-O—(2,3-dihydro-2,2-dimethyl-benzofuran-7-yl)ester |
| 5 | 2-butoxy-ethanol | 2,3-dihydro-2,2-dimethyl-7-hydroxy-benzofuran | C$_4$H$_9$—O—CH$_2$—CH$_2$ | 2,3-dihydro-2,2-dimethyl-benzofuran-7-yl | 2-chloro-ethyl-phosphonic acid-O—(2-butoxy-ethyl)-O—(2,3-dihydroxy-2,2-dimethyl-benzofuran-7-yl)-ester |
| 6 | sec.butanol | 2,3-dihydro-2,2-dimethyl-7-hydroxy-benzofuran | —CH$_3$—CH—CH$_2$— CH | 2,3-dihydro-2,2-dimethyl-benzofuran-7-yl | 2-chloro-ethyl-phosphonic acid-O—(2-methyl-propyl)-O—(2,3-dihydro-2,2-dimethyl-benzofuran-7-yl)-ester |
| 7 | — | 4-methyl-umbelliferon | H | 4-methyl-coumarin-7-yl | 2-chloro-ethyl-phosphonic acid-O—(4-methyl-coumarin-7-yl)-ester |
| 8 | methanol | 4-methyl-umbelliferon | CH$_3$ | 4-methyl-coumarin-7-yl | 2-chloro-ethyl-phosphonic acid-O—methyl-O—(4-methyl-coumarin-7-yl)-ester |
| 9 | methanol | 2,2,4-trimethyl-(2H)—5-hydroxy-chromene | CH$_3$ | 2,2,4-trimethyl-(2H)—chromene-5-yl | 2-chloro-ethyl-phosphonic acid-O—methyl-(2,2,4-trimethyl-(2H)—chromene-5-yl)-ester |
| 10 | methanol | 2,2,4-trimethyl-(2H)—7-hydroxy-chromene | CH$_3$ | 2,2,4-trimethyl-(2H)—chromene-7-yl | 2-chloro-ethyl-phosphonic acid-O—methyl-O—(2,2,4-trimethyl-(2H)—chromene-7-yl)-ester |

EXAMPLE 3

Emulsifiable concentrate can be prepared from the following components:

EXAMPLE 4

Emulsifiable concentrate:

| Compound No. 3 | 70% by mass |

| | |
|---|---|
| α-[4-(1,1,3,3-tetramethyl-butyl)-phenyl]-ω-hydroxy-poly(oxy-1,2-ethandiyl) (Triton X-100) | 10% by mass |
| isophoron | 20% by mass |
| | 100% by mass |

EXAMPLE 5

Wettable powder

| | |
|---|---|
| Compound No. 8 | 20% by mass |
| sodium-oleyl-methyl-tauride (Arkopon T-Hoechst) | 7% by mass |
| sodium-lignin-sulphonate | 5% by mass |
| colloidal synthetic silicon dioxyde | 28% by mass |
| kaolin | 40% by mass |
| | 100% by mass |

EXAMPLE 6

Dusting agent

| | |
|---|---|
| Compound No. 2 | 1% by mass |
| talc | 99% by mass |
| | 100% by mass |

EXAMPLE 7

Colloidal aqueous suspension concentrate

| | |
|---|---|
| Compound No. 10 | 30% by mass |
| mixture of polyoxyethylene-mono-laurate and alkylphenol-alkoxalates (Emulsogen IC-HOECHST) | 6% by mass |
| magnesium-lignin-sulphonate | 4% by mass |
| lecithine | 4% by mass |
| colloidal synthetic silicon dioxide | 26% by mass |
| water | 30% by mass |
| | 100% by mass |

EXAMPLE 8

Granule

| | |
|---|---|
| Compound No. 4 | 5% by mass |
| kaolin | 95% by mass |
| | 100% by mass |

EXAMPLE 9

Emulsifiable concentrate

| | |
|---|---|
| Compound No. 1 | 85% by mass |
| polyoxyethylene-sorbitan-monolaurate (Tween-20, Atlas) | 10% by mass |
| methylene-chloride | 5% by mass |
| | 100% by mass |

EXAMPLE 10

Water soluble concentrate

| | |
|---|---|
| Compound No. 12 | 10% by mass |
| polyoxyethylene-sorbitan-monolaurate (Tween-20, Atlas) | 8% by mass |
| water | 82% by mass |
| | 100% by mass |

EXAMPLE 11

Dusting agent

| | |
|---|---|
| Compound No. 15 | 1% by mass |
| talc | 99% by mass |
| | 100% by mass |

EXAMPLE 12

Wettable powder

| | |
|---|---|
| Compound No. 18 | 70% by mass |
| fatty alcohol sulphonate | 6% by mass |
| sodium-lignin-sulphonate | 4% by mass |
| colloidal synthetic silicon dioxide | 16% by mass |
| kaolin | 4% by mass |
| | 100% by mass |

EXAMPLE 13

Granule

| | |
|---|---|
| Compound No. 14 | 5% by mass |
| vermiculite | 95% by mass |
| | 100% by mass |

Biological tests

2-Chloroethyl-phosphonic acid esters and salts thereof according to the invention were tested on plant growth regulating activity in green house by using tomato, soya beans and sunflower as indicating plants. The plants were seeded into pots filled with turf or the plants were set as seedlings. The post-emergent treatment was carried out on tomato at a development stage of 20–30 cm. and on soybeans and sunflower at a development stage of 10–20 cm. In the course of the tests a control without active ingredient (K) was always used and as active ingredient 2-chloro-ethyl-phosphonic acid-O-methyl-O-(2,3-dihydro-2,2-dimethyl-benzofuran-7-yl)-ester (Compound No. 2) and as referential compounds 2-chloro-ethyl-phophonic acid (F) and 2,2-dimethyl-2,3-dihydro-7-hydroxy-benzofuran (G) were used. In the tomato indicating plant pre-emergent treatment was also carried out. The used doses and the obtained results are summarized in the tables.

When evaluating the biological tests the change of the height of plants was determined. The height change in the case of tomato treated post-emergence was determined on the 4., 7. and 10. day after the treatment, in soybeans and sunflower on the 7th day after the treatment and in case of the treatment pre-emergence, the plant's height was also determined on the 7th day after treatment.

The results are given in the percent of the starting height.

TABLE I

Effect of post-emergent treatment on the growth of tomato

| Composition | Treatment dose kg./ha. | Change in the % of the starting height | | |
|---|---|---|---|---|
| | | 4. day | 7. day | 10. day |
| K | | 29 | 53 | 71 |
| Compound 2 | 0.5 | 47 | 81 | 101 |
| | 1.0 | 47 | 77 | 100 |
| | 2.0 | 41 | 71 | 85 |
| F | 0.5 | 42 | 69 | 86 |
| | 1.0 | 41 | 68 | 76 |
| | 2.0 | 43 | 65 | 70 |
| G | 0.5 | 31 | 63 | 78 |
| | 1.0 | 37 | 62 | 80 |
| | 2.0 | 38 | 70 | 83 |

The table shows that 2-chloro-ethyl-phosphonic acid-O-methyl-(2,3-dihydro-2,2-dimethyl-benzofuran-7-yl)-ester increase the height of tomato at a great extent related to the untreated control. The increase of the height was in inverse ratio to the increase of the dose. At a rate of 2 kg./ha. its activity was the same as that of 2-kg./ha. 2,2-dimethyl-2,3-dihydro-7-hydroxy-benzofuran and that of 0.5 kg./ha. of 2-chloro-ethyl-phosphonic acid.

TABLE 2

Effect of post-emergent treatment on the growth of soybeans

| Composition | Treatment dose kg./ha. | Change in the % of the starting height | | | | | |
|---|---|---|---|---|---|---|---|
| | | I. rep. | II. rep. | III. rep. | IV. rep. | V. rep. | $\overline{X}$ |
| K | | 23.4 | 26.9 | 21.1 | 25.1 | 26.2 | 24.5 |
| Comp. 2 | 0.5 | 17.1 | 24.5 | 29.0 | 25.8 | 23.1 | 23.4 |
| | 1.0 | 14.9 | 24.5 | 24.0 | 23.1 | 17.1 | 20.7 |
| | 2.0 | 16.0 | 13.3 | 18.6 | 18.0 | 14.5 | 16.1 |
| F | 0.5 | 13.0 | 11.3 | 14.1 | 15.1 | 9.4 | 12.6 |
| | 1.0 | 15.1 | 10.6 | 12.4 | 11.4 | 11.4 | 12.2 |
| | 2.0 | 6.6 | 10.0 | 8.5 | 9.5 | 8.8 | 8.7 |
| G | 0.5 | 33.8 | 28.2 | 32.6 | 37.6 | 33.3 | 33.1 |
| | 1.0 | 22.6 | 30.4 | 35.8 | 22.1 | 33.8 | 28.9 |
| | 2.0 | 23.8 | 18.4 | 20.5 | 20.6 | 19.5 | 20.6 | rep. = repetition

The table shows that as opposed to the results on tomato a higher rate of (1.0, 2.0 kg./ha.) 2-chloro-ethyl-phosphonic acid-O-methyl-O-(2,3-dihydro-2,2-dimethyl-benzofuran-7-yl)-ester had a result of decreasing the height of soybeans. The extent of this decrease was lower than the values measured at similar rates of 2-chloro-ethyl-phosphonic acid. When using 2,2-dimethyl-2,3-dihydro-7-hydroxy-benzofuran alone the doses of 0.5 and 1.0 kg./ha intensively increased whereas the dose of 2 kg./ha. slightly decreased the growth.

TABLE 3

Effect of post-emergent treatment on the growth of sunflower

| Composition | Treatment dose kg./ha. | Change in the % of the starting height | | | | | |
|---|---|---|---|---|---|---|---|
| | | I. rep. | II. rep. | III. rep. | IV. rep. | V. rep. | $\overline{X}$ |
| K | | 33.0 | 38.8 | 31.1 | 27.9 | 26.7 | 31.5 |
| Compound 2 | 1.0 | 24.3 | 22.2 | 24.2 | 28.4 | 29.6 | 25.7 |
| | 2.0 | 21.2 | 17.0 | 20.0 | 20.5 | 21.5 | 20.0 |
| F | 1.0 | 6.3 | 5.0 | 6.1 | 5.4 | 6.2 | 5.8 |
| | 2.0 | 5.8 | 5.1 | 5.0 | 4.0 | 2.7 | 4.5 |
| G | 1.0 | 27.8 | 25.0 | 38.9 | 33.3 | 26.5 | 30.3 |
| | 2.0 | 32.9 | 35.0 | 35.3 | 30.1 | 30.2 | 32.7 |
| G + F | 0.5 + 0.5 | 18.9 | 17.4 | 17.3 | 23.5 | 20.5 | 19.5 |
| | 0.5 + 1.0 | 10.6 | 10.4 | 10.7 | 10.7 | 10.8 | 10.6 |
| | 1.0 + 0.5 | 20.2 | 25.5 | 21.3 | 15.7 | 23.6 | 21.3 |
| | 1.0 + 1.0 | 10.1 | 8.5 | 10.3 | 11.8 | 14.2 | 11.0 | rep. = repetition

Compared to the untreated control 1 kg./ha. of 2-chloroethyl-phosphonic acid-O-methyl-O-(2,3-dihydro-2,2-dimethyl-benzofuran-7-yl)-ester decreased the growth of sunflower by 1/6 and the dose of 2.0 kg./ha. decreased its height by approximately ⅓. As a result of similar doses of 2-chloro-ethyl-phosphonic acid the height growth amounted only to 1/6 of the value of the control.

2,2-Dimethyl-2,3-dihydro-7-hydroxy-benzofuran did not significantly influence the growth.

When using 2-chloro-ethyl-phosphonic acid and 2,2-dimethyl-(2,3-dihydro-7-hydroxy)-benzofuran in a mixture of various active ingredient ratios the depressant activity of 2-chloro-ethyl-phosphonic acid decreased. It further shows that by using an 1:1 mixture of the two compounds the depressant activity of 2-chloro-ethyl-phosphonic acid somewhat decreased.

TABLE 4

Effect of pre-emergent treatment on the growth of tomato

| Composition | Treatment dose kg./ha. | Change in the % of the starting height | | | | |
|---|---|---|---|---|---|---|
| | | I. rep. | II. rep. | III. rep. | IV. rep. | $\overline{X}$ |
| K | | 28.4 | 31.3 | 27.5 | 26.1 | 28.3 |
| Compound 2 | 1.0 | 28.6 | 29.5 | 30.7 | 31.6 | 30.1 |
| | 2.0 | 35.2 | 33.1 | 30.8 | 32.6 | 32.9 |
| | 4.0 | 26.2 | 24.5 | 26.3 | 25.2 | 25.6 |
| | 8.0 | 20.8 | 17.6 | 18.9 | 17.1 | 18.6 |
| F | 2.0 | 27.5 | 26.9 | 33.1 | 28.2 | 28.9 |
| G | 2.0 | 33.1 | 32.6 | 29.8 | 32.9 | 32.1 | rep.: repetition

When testing the activity of the compositions through the soil it can be observed that when spraying 2-chloro-ethyl-phosphonic acid on the soil no plant growth regulating activity is exhibited. A rate of 2 kg./ha. of 2,2-dimethyl-2,3-dihydro-7-hydroxy-benzofuran stimulated the growth similarly to 1 and 2 kg./ha. resp. of 2-chloro-ethyl-phosphonic acid-O-methyl-O-(2,3-dihydro-2,2-dimethyl-benzofuran-7-yl)-ester. The growth of tomato at a rate of 4 kg./ha. is moderate whereas at a rate of 8 kg./ha. the growth was reduced by ⅓.

In green house tests in culture dishes the plant growth regulating activity of 2-chloro-ethyl-phosphonic acid-O-methyl-O-(2,3-dihydro-2,2-dimethylbenzofuran-7-yl)-ester was tested pre-emergence and post-emergence by using tomato, soybeans and sunflowers as test plants.

The height of tomato was increased by using 2-chloro-ethyl-phosphonic acid-O-methyl-(2,3-dihydro-2,2-dimethyl-benzofuran-7-yl)-ester, the extent of the growth was in inverse ratio to the dose. The activity of the active ingredient depends on the tested arts and on the development stage of the plants. The height of the soybeans and the sunflowers was reduced by the doses used on tomato proportionally with the amount of the active ingredient used pro hectare.

2-Chloro-ethyl-phosphonic acid-O-methyl-O-(2,3-dihydro-2,2-dimethyl-benzofuran-7-yl)-ester as opposed to 2-chloro-ethyl-phosphonic acid when treated pre-emergence in tomato can act as plant growth regulator by being absorbed from the soil through the route.

The biological tests were repeated under the disclosed test conditions on the mentioned plants. As active ingredient 2-chloro-ethyl-phosphonic acid-O-methyl-(4-methyl-coumarin-7-yl)-ester (Compound No. 7) and as referential compounds 2-chloro-ethyl-phosphonic acid (F) and 7-hydroxy-4-methyl-coumarin (M) were used next to the control (K).

TABLE 5

Effect of post-emergence treatment on the growth of tomato

| Composition | Treatment dose kg./ha. | Change in the % of the starting height |  |  |
|---|---|---|---|---|
|  |  | 4. day | 7. day | 10. day |
| K |  | 29 | 53 | 71 |
| Compound No. 7 | 0.5 | 38 | 73 | 90 |
|  | 1.0 | 44 | 81 | 95 |
|  | 2.0 | 40 | 66 | 83 |
| F | 0.5 | 42 | 69 | 86 |
|  | 1.0 | 41 | 68 | 76 |
|  | 2.0 | 43 | 65 | 70 |
| M | 0.5 | 33 | 60 | 72 |
|  | 1.0 | 35 | 64 | 78 |
|  | 2.0 | 37 | 70 | 82 |

The results of Table 5 show that 2-chloro-ethyl-phosphonic acid-O-methyl-(4'-methyl-coumarin-7'-yl)-ester significantly increased the growth of the tomato related to the untreated control. The activity can be characterized as a function of the dose by a curve of second order the peak of which is at the dose of 1 kg./ha. By further increasing the dose the composition already shows mainly a growth inhibiting activity. It can be seen further that the growth stimulating activity is more intensive than that of 7-hydroxy-4-methyl-coumarin and at higher doses the growth inhibiting activity is lower than that of 2-chloro-ethyl-phosphonic acid.

TABLE 6

Effect of post-emergent treatments on the growth of soybeans

| Composition | Treatment dose kg./ha. | Change in the % of starting height |  |  |  |  |  |
|---|---|---|---|---|---|---|---|
|  |  | I. | II. | III. | IV. | V. | Average |
| K |  | 23.4 | 26.9 | 21.1 | 25.1 | 26.2 | 24.5 |
| Compound No. 7 | 0.5 | 18.2 | 22.4 | 26.0 | 22.4 | 23.6 | 22.5 |
|  | 1.0 | 19.3 | 21.1 | 22.6 | 20.8 | 21.2 | 21.0 |
|  | 2.0 | 15.4 | 13.2 | 15.7 | 16.0 | 15.1 | 15.1 |
| F | 0.5 | 13.0 | 11.3 | 14.1 | 15.1 | 9.4 | 12.6 |
|  | 1.0 | 15.1 | 10.6 | 12.4 | 11.4 | 11.4 | 12.2 |
|  | 2.0 | 6.6 | 10.0 | 8.5 | 9.5 | 8.8 | 8.7 |
| M | 0.5 | 30.7 | 31.0 | 31.5 | 33.2 | 35.4 | 32.4 |
|  | 1.0 | 24.2 | 30.1 | 30.2 | 24.1 | 29.8 | 27.7 |
|  | 2.0 | 21.9 | 19.0 | 20.0 | 20.2 | 18.7 | 20.0 |

When using 2-chloro-ethyl-phosphonic acid-O-methyl-O-(4'-methyl-coumarin-7'-yl)-ester in soybeans all the three tested doses reduced the height of soybeans differently from the results observed on tomato. The extent of the reduction of the height was lower than the values measured for 2-chloro-ethyl-phosphonic acid with similar rates. 0.5 kg./ha. of 7-hydroxy-4-methyl-coumarin stimulated whereas 2 kg./ha. of the same coumpound inhibited the growth.

TABLE 7

Effect of post-emergent treatments on the growth of sunflower

| Composition | Treatment dose kg./ha. | Change in the % of starting the height |  |  |  |  |  |
|---|---|---|---|---|---|---|---|
|  |  | I. | II. | III. | IV.. | V. | Average |
| K |  | 33.0 | 38.8 | 31.1 | 27.9 | 26.7 | 31.5 |
| Compound No. 7 | 1.0 | 22.1 | 20.8 | 23.0 | 24.1 | 23.7 | 22.7 |
|  | 2.0 | 19.3 | 17.6 | 20.1 | 18.9 | 21.1 | 19.4 |
| F | 1.0 | 6.3 | 5.0 | 6.1 | 5.4 | 6.2 | 5.8 |
|  | 2.0 | 5.8 | 5.1 | 5.0 | 4.0 | 2.7 | 4.5 |
| M | 1.0 | 31.3 | 34.6 | 29.8 | 30.5 | 32.4 | 31.7 |
| M | 2.0 | 27.4 | 28.2 | 27.5 | 26.9 | 28.1 | 27.6 |
| M + F | 0.5 + 0.5 | 20.3 | 19.8 | 21.0 | 19.5 | 20.4 | 20.2 |
|  | 1.0 + 0.5 | 9.9 | 10.4 | 9.2 | 9.5 | 10.0 | 9.8 |
|  | 0.5 + 1.0 | 21.4 | 25.0 | 22.0 | 21.3 | 24.2 | 22.8 |
|  | 1.0 + 1.0 | 9.5 | 9.1 | 10.6 | 10.2 | 11.4 | 10.2 |

When compared with the untreated control 2-chloro-ethyl-phosphonic acid-O-methyl-O-(4-methyl-coumarin-7-yl)-ester reduced the growth of sunflower at both of the tested doses. The plant growth was intensively inhibited by 2-chloro-ethyl-phosphonic acid whereas 1 kg./ha. of 7-hydroxy-4-methyl-coumarin did not effect the growth of sunflower and 2 kg./ha. of the same compound slightly inhibited its growth. A mixture of 2-chloro-ethyl-phosphonic acid and 7-hydroxy-4-methyl-coumarin at various active ingredient's ratios it could be observed that the depressant activity of 2-chloro-ethyl-phosphonic acid was moderated by the 7-hydroxy-4-methyl-coumarin.

TABLE 8

Effect of pre-emergent treatment on the growth of tomato

| Composition | Treatment dose kg./ha. | Change in the % of the starting height |  |  |  |  |
|---|---|---|---|---|---|---|
|  |  | I. | II. | III. | IV. | Average |
| K |  | 28.4 | 31.3 | 27.5 | 26.1 | 28.3 |
| Compound No. 7 | 1.0 | 32.1 | 33.6 | 30.8 | 31.5 | 32.0 |
|  | 2.0 | 35.8 | 36.1 | 33.4 | 34.1 | 34.9 |
|  | 4.0 | 27.2 | 25.1 | 25.8 | 24.7 | 25.2 |
|  | 8.0 | 17.4 | 19.2 | 17.6 | 17.0 | 17.8 |
| F | 2.0 | 27.5 | 26.9 | 33.1 | 28.2 | 28.9 |
| M | 2.0 | 30.1 | 34.6 | 30.8 | 32.9 | 32.1 |

When evaluating the activity of the compositions through the soil it shows that 2-chloro-ethyl-phosphonic acid does not act as plant growth regulator through the roots.

2kg./ha. of 7-hydroxy-4-methyl-coumarin stimulated the growth similarly to 1 and 2 kg./ha. of 2-chloro-ethyl-phosphonic acid-O-methyl-O-(4-methyl-coumarin-7-yl)-ester. By increasing the dose pro hectare to 4 and 8 kg./ha. the growth of tomato was already moderated.

When spraying 2-chloro-methyl-phosphonic acid-O-methyl-O-(4'-methyl-coumarin-7-yl)-ester on the foliage the height of tomato was increased. The growth of soybeans and sunflowers at the tested doses was reduced by the active ingredient.

When treating tomato pre-emergence 2-chloro-ethyl-phosphonic acid-O-methyl-O-(4'-methyl-coumarin-7'-yl)-ester was sprayed on the soil and the active ingredient penetrated through the root of the plants and acted as plant growth regulator which could be observed in the change of the height of tomato.

Under the given test conditions further biological tests were carried out on the mentioned test plants. As active ingredient 2-chloro-ethyl-phosphonic acid-O-(2,3-dihydro-2,2-dimethyl-benzofuran-7-yl)-ester and as referential compounds 2-chloro-ethyl-phosphonic acids (F) and 2,3-dihydro-2,2-dimethyl-7-hydroxy-benzofuran (N) were used next to the control (K).

TABLE 9

Effect of post-emergent treatments on the growth of soybeans

| Composition | Treatment dose kg./ha. | I. | II. | III. | IV. | V. | Average |
|---|---|---|---|---|---|---|---|
| K |  | 23.4 | 26.9 | 21.1 | 25.1 | 26.2 | 24.5 |
| Comp. No. 1 | 0.5 | 14.9 | 15.1 | 13.6 | 14.8 | 14.1 | 14.5 |
|  | 1.0 | 13.7 | 14.0 | 14.6 | 14.1 | 13.8 | 14.0 |
|  | 2.0 | 13.1 | 13.5 | 12.9 | 13.6 | 13.0 | 13.2 |
| F | 0.5 | 13.0 | 11.3 | 14.1 | 15.1 | 9.4 | 12.6 |
|  | 1.0 | 15.1 | 10.6 | 12.4 | 11.4 | 11.4 | 12.2 |
|  | 2.0 | 6.6 | 10.0 | 8.5 | 9.5 | 8.8 | 8.7 |
| N | 0.5 | 33.8 | 28.2 | 32.6 | 37.6 | 33.3 | 33.1 |
|  | 1.0 | 22.6 | 30.4 | 35.8 | 22.1 | 33.8 | 28.9 |
|  | 2.0 | 23.8 | 18.4 | 20.5 | 20.6 | 19.5 | 20.6 |

After the evaluation of the biological activity of 2-chloro-ethyl-phosphonic acid-O-(2,3-dihydro-2,2-dimethyl-benzofuran-7-yl)-ester it shows that the soybeans' growth is influenced by the compound. In the tested period the height of the untreated plants increased on an average by 24.5% whereas the height of the plants treated by various doses of 2-chloro-ethyl-phosphonic acid-O-(2,3-dihydro-2,2-dimethyl-benzofuran-7-yl)-ester by 13%.

TABLE 10

Effect of post-emergent treatment on the growth of sunflower

| Composition | Treatment dose kg./ha. | I. | II. | III. | IV. | V. | Average |
|---|---|---|---|---|---|---|---|
| K |  | 33.0 | 38.8 | 31.1 | 27.9 | 26.7 | 31.5 |
| Comp. No. 1 | 1.0 | 8.7 | 10.3 | 9.4 | 9.7 | 10.0 | 9.6 |
|  | 2.0 | 7.5 | 6.6 | 8.0 | 6.4 | 7.0 | 7.1 |
| F | 1.0 | 6.3 | 5.0 | 6.1 | 5.4 | 6.2 | 5.8 |
|  | 2.0 | 5.8 | 5.1 | 5.0 | 4.0 | 2.7 | 4.5 |
| N | 1.0 | 27.8 | 25.0 | 38.9 | 33.3 | 26.5 | 30.3 |
|  | 2.0 | 32.9 | 35.0 | 35.3 | 30.1 | 30.2 | 32.7 |
| N + F | 0.5 + 0.5 | 18.9 | 17.4 | 17.3 | 23.5 | 20.5 | 19.5 |
|  | 0.5 + 1.0 | 10.6 | 10.4 | 10.7 | 10.7 | 10.8 | 10.6 |
|  | 1.0 + 0.5 | 20.2 | 25.5 | 21.3 | 15.7 | 23.6 | 21.3 |
|  | 1.0 + 1.0 | 10.1 | 8.5 | 10.3 | 11.8 | 14.2 | 11.0 |

The growth of sunflower was significantly reduced by 2-chloro-ethyl-phosphonic acid-O-(2,3-dihydro-2,2-dimethyl-benzofuran-7-yl)-ester when comparing with the untreated control. During the test period the height of the untreated control was increased by 31.5% related to the starting value whereas the height of the plants treated with the compound according to the invention was increased only by 9.6–7.1%. The compounds were used in combinations of various ratios thus 2-chloro-ethyl phosphonic acid and 2,3-dihydro-2,2-dimethyl-7-hydroxy-benzofuran were used at rates of 1 kg./ha.+0.5 kg./ha. and 1 kg./ha.+1 kg./ha. and none of these combinations achieved the plant growth regulating activity of the compound according to the invention.

TABLE 11

Effect of pre-emergent treatments on the growth of tomato

| Composition | Treatment dose kg./ha. | I. | II. | III. | IV. | Average |
|---|---|---|---|---|---|---|
| K |  | 28.4 | 31.3 | 27.5 | 26.1 | 28.3 |
| Compound No. 1 | 1.0 | 38.6 | 40.2 | 37.9 | 38.3 | 38.8 |
|  | 2.0 | 43.2 | 41.8 | 42.0 | 39.6 | 41.2 |
|  | 4.0 | 41.7 | 44.6 | 43.9 | 42.7 | 43.2 |

TABLE 11-continued

Effect of pre-emergent treatments on the growth of tomato

| Composition | Treatment dose kg./ha. | I. | II. | III. | IV. | Average |
|---|---|---|---|---|---|---|
|  | 8.0 | 21.4 | 19.6 | 24.3 | 20.5 | 21.5 |
| F | 2.0 | 27.5 | 26.9 | 33.1 | 28.2 | 28.9 |
| N | 2.0 | 33.1 | 32.6 | 29.8 | 32.9 | 32.1 |

2-Chloro-ethyl-phosphonic acid-O-(2,3-dihydro-2,2-dimethyl-benzofuran-7-yl)-ester was used pre-emergence and when evaluating the biological activity of the compound an intensive plant growth stimulating activity can be seen on tomato showing the composition was absorbed by the plant from the soil. The growth of the untreated control was in the tested period 28.3% related to the starting height. The growth of the plants treated with 1–4 kg./ha. of 2-chloro-ethyl-phosphonic acid-O-(2,3-dihydro-2,2-dimethyl-benzofuran-7-yl)-ester was 38.8–43.2%. By increasing the dose of the composition to 8 kg./ha. the growth stimulation turned over to growth inhibition. The test results can be summarized as follows:

By spraying 2-chloro-ethyl-phosphonic acid-O-(2,3-dihydro-2,2-dimethyl-benzofuran-7-yl)-ester on soybeans and sunflower a significant growth inhibition could be observed related to the untreated control. On the basis of the growth inhibition it can be said that 2-chloro-ethyl-phosphonic acid-(2,3-dimethyl-benzofuran-7-yl)-ester regulates the plant growth when used post-emergence. In case of a treatment pre-emergence the plant growth regulating activity of 2-chloro-ethyl-phosphonic acid-O-(2,3-dihydro-2,2-dimethyl-benzofuran-7-yl)-ester can be similarly observed as proved by the tests carried out e.g. on tomatoe.

The post-emergent activity of the compositions according to the invention was also tested in free land tests on soybeans, maize, winter wheat and red pepper. The results of the test are shown in the following tables.

SOYBEANS

Test conditions

Type of soil: field chernozem
Green-crop: sugar beet
Fertilization:
  50 kg./ha. N(ammonium-nitrate)
  100 kg./ha. $P_2O_5$ (superphosphate of 18%)
  120 kg./ha. $K_2O$ (potassium chloride of 50%)
Weed killing: 910 g./ha. 2,6-dinitro-N,N-dipropyl-4-trifluoro-methyl-aniline+900 g./ha. N-(4-bromo-3-chloro-phenyl)-N'-methoxy-N'-methyl-urea
Art: ISz-15
Stock-number: 350,000 stock/ha.
Parcel size: 2×10 m.
Repetitions: 6
Spray liquid: 200 l./ha.
Treatments:
  (1) untreated control
  (2) 2-chloroethyl-phosphonic acid: 250 g./ha.
  (3) 2-chloroethyl-phosphonic acid: 500 g./ha.
  (4) 2-chloroethyl-phosphonic acid: 1000 g./ha.
  (5) 2-chloroethyl-phosphonic acid-O-(2,3-dihydro-2,2-dimethyl-benzofuran-7-yl)-ester: 250 g./ha.
  (6) 2-chloroethyl-phosphonic acid-O-(2,3-dihydro-2,2-dimethyl-benzofuran-7-yl)-ester: 500 g./ha.
  (7) 2-chloroethyl-phosphonic acid-O-(2,3-dihydro-2,2-dimethyl-benzofuran-7-yl)-ester: 1000 g./ha.

(8) 2-chloroethyl-phosphonic acid-O-methyl-O-(4'-methyl-coumarin-7'-yl)ester: 250 g./ha.
(9) 2-chloroethyl-phosphonic acid-O-methyl-O-(4'-methyl-coumarin-7'-yl)-ester: 500 g./ha.
(10) 2-chloroethyl-phosphonic acid-O-methyl-O-(4'-methyl-coumarin-7'-yl)-ester: 1000 g./ha.

The spraying was carried out at the beginning of the budding of the soybeans. The spray liquid concentration changed in the range of 1.13 g./l. to 4.54 g./l. related to the active ingredient.

Compositions disclosed in Examples 3 and 8 were used.

TABLE 12
Effect of post-emergent treatment on soybeans' crop

| Number of treament | Dose g./ha. | Crop average t./ha. | Change in the % of the control |
|---|---|---|---|
| 1. | — | 2.60 | 100 |
| 2 | 250 | 2.68 | 103 |
| 3 | 500 | 2.32 | 89 |
| 4 | 1000 | 2.05 | 79 |
| 5 | 250 | 3.00 | 115 |
| 6 | 500 | 2.90 | 111 |
| 7 | 1000 | 2.74 | 105 |
| 8 | 250 | 2.98 | 115 |
| 9 | 500 | 3.00 | 115 |
| 10 | 1000 | 2.82 | 108 |

The results show that the compounds according to the invention increased the crop as opposed to 2-chloro-ethyl-phosphonic acid.

A 15% crop increase was measured at a rate of 250 g./ha. 2-chloro-ethyl-phosphonic acid-O-(2,3-dihydro-2,2-dimethyl-benzofuran-7-yl)-ester and 2-chloro-ethyl-phosphonic acid-O-methyl-O-(4-methyl-coumarin-7-yl)-ester. By increasing the dose to 1000 g./ha. the crop increase amounted only to 5–8%, the crop, however, was reduced to 21% by the same dose of 2-chloro-ethyl-phosphonic acid.

WINTER WHEAT

Test conditions

Type of soil: field chernozem
Green-crop: green peas
Fertilization:
  200 kg./ha. N(ammonium-nitrate)
  120 kg./ha. $P_2O_5$ (superphosphate of 18%)
  140 kg./ha. $K_2O$ (potassium chloride of 50%)
Weed killing: 1000 g./ha. ammonium salt of 2,4-dichloro-phenoxy-acetic acid
Art: Mv-80
Stock number: 5.5 million stock/ha.
Parcel size: 2×10 m.
Repetitions: 6
Spray liquid: 220 l./ha.
Treatments:
  (1) untreated control
  (2) 2-chloroethyl-phosphonic acid: 500 g./ha.
  (3) 2-chloroethyl-phosphonic acid: 1000 g./ha.
  (4) 2-chloroethyl-phosphonic acid: 2000 g./ha.
  (5) 2-chloroethyl-phosphonicaacid-O-(2,3-dihydro-2,2-dimethyl-benzofuran-7-yl)-ester: 500 g./ha.
  (6) 2-chloroethyl-phosphonic acid-O-(2,3-dihydro-2,2-dimethyl-benzofuran-7-yl)-ester: 1000 g./ha.
  (7) 2-chloroethyl-phosphonic acid-O-(2,3-dihydro-2,2-dimethyl-benzofuran-7-yl)-ester: 2000 g./ha.
  (8) 2-chloroethyl-phosphonic acid-O-methyl-O-(4'-methyl-coumarin-7'-yl)-ester: 500 g./ha.
  (9) 2-chloroethyl-phosphonic acid-O-methyl-O-(4'-methyl-coumarin-7'-yl)ester: 1000 g./ha.
  (10) 2-chloroethyl-phosphonic acid-O-methyl-O-(4'-methyl-coumarin-7'-yl)-ester: 2000 g./ha.
  (11) 2-chloroethyl-phosphonic acid: 50 g./ha.
  (12) 2-chloroethyl-phosphonic acid: 100 g./ha.
  (13) 2-chloroethyl-phosphonic acid: 200 g./ha.
  (14) 2-chloroethyl-phosphonic acid-O-(2,3-dihydro-2,2-dimethyl-benzofuran-7-yl)-ester: 50 g./ha.
  (15) 2-chloroethyl-phosphonic acid-O-(2,3-dihydro-2,2-dimethyl-benzofuran-7-yl)-ester: 100 g./ha.
  (16) 2-chloroethyl-phosphonic acid-O-(2,3-dihydro-2,2-dimethyl-benzofuran-7-yl)-ester: 200 g./ha.
  (17) 2-chloroethyl-phosphonic acid-O-methyl-O-(4'-methyl-coumarin-7'-yl)-ester: 50 g./ha.
  (18) 2-chloroethyl-phosphonic acid-O-methyl-O-(4'-methyl-coumarin-7'-yl)-ester: 100 g./ha.
  (19) 2-chloroethyl-phosphonic acid-O-methyl-O-(4'-methyl-coumarin-7'-yl)-ester: 200 g./ha.

Treatments number 2 to 10 were performed when growing into thick and treatments 11–19 were performed during earing. The spray liquid concentration changed in the range of 0.22 g./l. to 9.1 g./l. related to the active ingredient. Compositions disclosed in Examples 3 and 8 were used.

TABLE 13
Effect of post-emergent treatments on the crop of winter wheat

| Number of treatment | Dose g./ha. | Crop average t./ha. | Change in the % of the control |
|---|---|---|---|
| 1 | — | 7.75 | 100 |
| 2 | 500 | 7.82 | 101 |
| 3 | 1000 | 7.53 | 97 |
| 4 | 2000 | 6.79 | 87 |
| 5 | 500 | 8.66 | 112 |
| 6 | 1000 | 8.51 | 110 |
| 7 | 2000 | 8.46 | 109 |
| 8 | 500 | 8.80 | 114 |
| 9 | 1000 | 8.97 | 116 |
| 10 | 2000 | 8.88 | 115 |
| 11 | 50 | 7.74 | 100 |
| 12 | 100 | 7.88 | 102 |
| 13 | 200 | 7.44 | 96 |
| 14 | 50 | 7.91 | 102 |
| 15 | 100 | 8.38 | 108 |
| 16 | 200 | 8.17 | 105 |
| 17 | 50 | 7.86 | 101 |
| 18 | 100 | 8.30 | 107 |
| 19 | 200 | 8.53 | 110 |

The data of the results performed on winter wheat show that when spraying the compositions according to the invention when growing into thick the crop was increased at the tested ratios by more than 10%. The crop was not influenced by 2-chloro-ethyl-phosphonic acid or it was reduced by higher rates of the same compound. When using the compositions according to the invention during the earing and 5–10% crop increase was measured at rates of 100–200 g./ha. At the same time 2-chloro-ethyl-phosphonic acid was applied and substantially no change in the crop could be observed.

MAIZE

Test conditions

Soil type: field chernozem
Green-crop: winter wheat
Fertilization:
  250 kg./ha. N(ammonium-nitrate)
  140 kg./ha. $P_2O_5$ (18% superphosphate)
  180 kg./ha. $K_2O$ (50% potassium chloride)

Weed killing: 2000 g./ha. N-(ethoxy-methyl)-2-ethyl-6-methyl-chloro-acetanilide + 1000 g./ha. N-(4-bromo-3-chloro-phenyl)-N'-methoxy-N'-methyl-urea
Art: Pioneer 3709
Stock number: 82,000 stock/ha.
Parcel size: 2.1 × 10 m.
Repetition: 6
Spray liquid: 220 l./ha.
Treatments:
  (1) Untreated control
  (2) 2-chloroethyl-phosphonic acid: 500 g./ha.
  (3) 2-chloroethyl-phosphonic acid-O-(2,3-dihydro-2,2-dimethyl-benzofuran-7-yl)-ester: 250 g./ha.
  (4) 2-chloroethyl-phosphonic acid-O-(2,3-dihydro-2,2-dimethyl-benzofuran-7-yl)-ester: 500 g./ha.
  (5) 2-chloroethyl-phosphonic acid-O-(2,3-dihydro-2,2-dimethyl-benzofuran-7-yl)-ester: 1000 g./ha.
  (6) 2-chloroethyl-phosphonic acid-O-methyl-O-(4'-methyl-coumarin-7'-yl)-ester: 250 g./ha.
  (7) 2-chloroethyl-phosphonic acid-O-methyl-O-(4'-methyl-coumarin-7'-yl)-ester: 500 g./ha.
  (8) 2-chloroethyl-phosphonic acid-O-methyl-O-(4'-methyl-coumarin-7'-yl)-ester: 1000 g./ha.

The treatments were performed at the stage of 6-8 leaves, the spray liquid concentration was in the range of 1.13 g./l. to 4.54 g./l. related to the active ingredient. Compositions disclosed in Examples 3 and 8 were used.

TABLE 14

Effect of post-emergent treatment on the crop of maize

| Number of treatment | Dose g./ha. | Crop average t./ha. | Change in the % of the control |
|---|---|---|---|
| 1 | — | 7.12 | 100 |
| 2 | 500 | 5.68 | 80 |
| 3 | 250 | 8.30 | 117 |
| 4 | 500 | 7.94 | 112 |
| 5 | 1000 | 6.97 | 98 |
| 6 | 250 | 8.56 | 120 |
| 7 | 500 | 8.03 | 113 |
| 8 | 1000 | 7.21 | 101 |

2-Chloroethyl-phosphonic acid-O-(2,3-dihydro-2,2-dimethyl-benzofuran-7-yl)-ester and 2-chloro-ethyl-phosphonic acid-O-methyl-O-(4'-methyl-coumarin-7'-yl)-ester were tested on maize and the crop was increased by 17-20% at a rate of 250 g./ha. By increasing the dose the crop increase was reduced and at a rate of 1000 g./ha. there was no more difference related to the untreated control. As opposed to the compounds according to the invention 500 g./ha. of 2-chloro-ethyl-phosphonic acid reduced the crop by 20%.

RED PEPPER

Test conditions

Soil type: field chernozem
Green crop: onion
Fertilization: 40 t./ha. organic fertilizer
Weed killing: 910 g./ha. 2,6-dinitro-N,N-dipropyl-4-trifluoro-methyl-aniline + manual hoeing
Art: Szegedi spicy F 03 red pepper
Stock number: 365,000 stock/ha.
Parcel size: 2×10 m.
Repetition: 6
Spray liquid: 220 l./ha.
Treatments:
  (1) Untreated control
  (2) 2-chloroethyl-phosphonic acid: 1000 g./ha.
  (3) 2-chloroethyl-phosphonic acid-O-(2,3-dihydro-2,2-dimethyl-benzofuran-7-yl)-ester: 1000 g./ha.
  (4) 2-chloroethyl-phosphonic acid-O-methyl-(4'-methyl-coumarin-7'-yl)-ester: 1000 g./ha.

The spraying was performed at the beginning of the colourization of the pepper. The spray liquid concentration amounted to 4.54 g./l, related to the active ingredient. Compositions disclosed in Examples 3 and 8 were used.

TABLE 15

Effect of post-emergent treatment on the crop and qualitative parameters of red pepper

| Composition, number of treatment | Crop t./h. | Crop % | Ratio of green peppers % | Dye % | The colour distribution of ripe peppers % completely ripe | semi-ripe | worthless |
|---|---|---|---|---|---|---|---|
| 1 | 3.15 | 100 | 28 | 8.84 | 42.5 | 22.6 | 43.8 |
| 2 | 2.85 | 90 | 25 | 10.07 | 51.2 | 28.4 | 20.4 |
| 3 | 3.55 | 113 | 20 | 9.98 | 70.1 | 11.4 | 18.5 |
| 4 | 3.60 | 114 | 20 | 9.65 | 72.3 | 9.7 | 18.0 |

According to the test results carried out on red pepper the compounds according to the invention increased the crop by 13-14% whereas the treatment with 2-chloro-ethyl-phosphonic acid reduced the crop. The ratio of completely green peppers was also less. The amount of colouring substances was increased related to the untreated control but did not achieve the value measured for 2-chloro-ethyl-phosphonic acid.

When testing the coloured peppers it shows that the ratio of the completely ripe peppers giving the best quality achieved 70% on parcels treated with the compounds according to the invention. The ratio of semi-ripe and brown worthless peppers was significantly lower than in case of the untreated control or on parcels treated with 2-chloro-ethyl-phosphonic acid.

We claim:

1. 2-Chloro-ethyl-phosphonic acid esters of the general Formula (I)

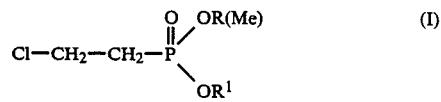

wherein

R stands for hydrogen, $C_{1-8}$ straight or branched chained alkyl, $C_{1-4}$ haloalkyl, $C_{1-4}$ alkoxy-$C_{1-2}$ alkyl, $R^1$ stands for 2,3-dihydro-2,2-dimethyl-benzofuran-7-yl, 4-methyl-coumarin-7-yl, 2,2,4-trimethyl-(2H)-chromen-5-yl or 2,2,4-trimethyl-(2H)-chromen-7-yl and Me stands for a monovalent cation and represents the salt of the acid.

2. 2-Chloro-ethyl-phosphonic acid-O-(2,3-dihydro-2,2-dimethyl-benzofuran-7-yl)-ester.

3. 2-Chloroethyl-phosphonic acid-O-(4'-methyl-coumarin-7'-yl)-ester.

4. 2-Chloro-ethyl-phosphonic acid-O-methyl-O-(2,3-dihydro-2,2-dimethyl-benzofuran-7-yl)-ester.

5. Plant growth regulating compositions containing as active ingredient 2-chloro-ethyl-phosphonic acid derivative of the general formula I of claim 1 wherein
R stands for hydrogen, $C_{1-8}$ straight or branched chained alkyl, $C_{1-4}$ haloalkyl, $C_{1-4}$ alkoxy-$C_{1-2}$ alkyl,
$R^1$ stands for 2,3-dihydro-2,2-dimethyl-benzofuran-7-yl, 4-methyl-coumarin-7-yl, 2,2,4-trimethyl-(2H)-chromen-5-yl or 2,2,4-trimethyl-(2H)-chromen-7-yl and Me stands for a monovalent cation
together with solid and/or liquid carriers and optionally surfactants.

6. Method of treatment of plants pre or post emergence comprising applying an effective amount of a compound of the general formula (I) as claimed in claim 1 to the plants or its surroundings.

* * * * *